(12) United States Patent
Vakkalanka

(10) Patent No.: US 11,103,488 B2
(45) Date of Patent: *Aug. 31, 2021

(54) METHODS OF TREATING AUTOIMMUNE, RESPIRATORY AND INFLAMMATORY DISORDERS BY INHALATION OF ROFLUMILAST N-OXIDE

(71) Applicant: Incozen Therapeutics Pvt. Ltd., Hyderabad (IN)

(72) Inventor: Swaroop K. Vakkalanka, Hyderabad (IN)

(73) Assignee: INCOZEN THERAPEUTICS PVT. LTD., Hyderabad (IN)

( * ) Notice: Subject to any disclaimer, the term of this patent is extended or adjusted under 35 U.S.C. 154(b) by 134 days.

This patent is subject to a terminal disclaimer.

(21) Appl. No.: 15/469,243

(22) Filed: Mar. 24, 2017

(65) Prior Publication Data

US 2017/0196843 A1    Jul. 13, 2017

Related U.S. Application Data

(63) Continuation of application No. 14/166,463, filed on Jan. 28, 2014, now Pat. No. 9,649,302.

(30) Foreign Application Priority Data

Jan. 28, 2013   (IN) .............................. 354/CHE/2013
Jan. 28, 2013   (IN) .............................. 355/CHE/2013

(51) Int. Cl.
| | |
|---|---|
| *A61K 31/44* | (2006.01) |
| *A61K 9/14* | (2006.01) |
| *A61K 9/51* | (2006.01) |
| *A61K 9/00* | (2006.01) |
| *A61K 45/06* | (2006.01) |

(52) U.S. Cl.
CPC ............ *A61K 31/44* (2013.01); *A61K 9/0073* (2013.01); *A61K 9/0075* (2013.01); *A61K 9/14* (2013.01); *A61K 45/06* (2013.01)

(58) Field of Classification Search
CPC .......... A61K 31/44; A61K 9/007; A61K 9/14; A61K 9/0073; A61K 9/0075; A61K 9/51
See application file for complete search history.

(56) References Cited

U.S. PATENT DOCUMENTS

| | | | |
|---|---|---|---|
| 7,175,854 B2* | 2/2007 | Dietrich | ............... A61K 9/1617 424/464 |
| 8,349,858 B2 | 1/2013 | Tulshian et al. | |
| 9,649,302 B2* | 5/2017 | Vakkalanka | ............ A61P 11/02 |
| 2004/0034087 A1 | 2/2004 | Kilian et al. | |
| 2006/0270667 A1 | 11/2006 | Pieper et al. | |
| 2007/0196285 A1* | 8/2007 | Maus | ................... A61K 31/167 424/46 |
| 2007/0254928 A1 | 11/2007 | Wollin et al. | |
| 2008/0317862 A1 | 12/2008 | Collingwood et al. | |

FOREIGN PATENT DOCUMENTS

| | | |
|---|---|---|
| EA | 200702201 A1 | 4/2008 |
| WO | WO-9501338 A1 | 1/1995 |
| WO | WO-2001090076 A1 | 11/2001 |
| WO | WO-2004047829 A1 | 6/2004 |
| WO | WO-2004084894 A1 | 10/2004 |
| WO | WO-2005082361 A1 | 9/2005 |
| WO | WO-2006094942 A1 | 9/2006 |
| WO | WO-2007071313 | 6/2007 |
| WO | WO-2011163469 A1 | 12/2011 |

OTHER PUBLICATIONS

International Search Report and Written Opinion issued in PCT/IB2014/058617 dated Apr. 7, 2014.
Bundschuh, et al., In Vivo Efficacy in Airway Disease Models of Roflumilast, a Novel Orally Active PDE4 Inhibitor, The Journal of Pharmacology and Experimental Therapeutics, 2001, 297:280-290.
Chapman, et al., Effect of Inhaled Roflumilast on the Prevention and Resolution of Allergen-Induced Late Phase Airflow Obstruction in Brown Norway Rats, European Journal of Pharmacology, 2007, 571:215-221.
Prescribing Information for Daliresp (foflumilast) tablets (Feb. 2011).
Beghe, et al., Phosphodiesterase-4 Inhibitor Therapy for Lung Diseases, Pulmonary Perspectives, American Journal of Respiratory and Critical Care Medicine, 2013, 188:271-278.
Kuss, et al., In Vivo Efficacy in Airway Disease Models of N-(3,5-Dichloropyrid-4-yl)-1[1-(4-fluorobenzyl)-5-hydroxy-indole-3-yl]-glyoxylic Acid Amide (AWD 12-281), a Selective Phosphodiesterase 4 Inhibitor for Inhaled Administration. The Journal of Pharmacology and Experimental Therapeutics, 2014, 307:1:373-385.
Bielekova et al., Mult Scler. Oct. 2009; 15(10): 1206-1214. doi:10.1177/1352458509345903.
Prescribing information for Daliresp® (2015).

* cited by examiner

*Primary Examiner* — Theodore R. Howell
(74) *Attorney, Agent, or Firm* — Blank Rome LLP

(57) ABSTRACT

The present disclosure relates to pharmaceutical compositions useful for (and to a method of) treating autoimmune, respiratory and/or inflammatory diseases and conditions. The method involves administering to a subject in need thereof roflumilast N-oxide by inhalation. The present disclosure particularly relates to the treatment of asthma and chronic obstructive pulmonary disease (COPD) by administering roflumilast N-oxide by inhalation.

25 Claims, 5 Drawing Sheets

METHODS OF TREATING AUTOIMMUNE, RESPIRATORY AND INFLAMMATORY DISORDERS BY INHALATION OF ROFLUMILAST N-OXIDE

The present application is a continuation of U.S. patent application Ser. No. 14/166,463, filed Jan. 28, 2014, which claims the benefit of Indian Patent Application Nos. 354/CHE/2013, filed Jan. 28, 2013, and 355/CHE/2013, filed Jan. 28, 2013, each of which is hereby incorporated by reference in its entirety.

FIELD OF THE INVENTION

The present invention relates to a method of treating an autoimmune, respiratory and/or inflammatory disease or condition, such as asthma, COPD and other allergic and/or inflammatory disorders of the lung by pulmonary administration (e.g., by inhalation) of roflumilast N-oxide or a pharmaceutically acceptable salt thereof. The invention also relates to pharmaceutical compositions for use in the method.

BACKGROUND OF THE INVENTION

Autoimmune, respiratory and inflammatory diseases such as chronic obstructive pulmonary disorder (COPD) and asthma are chronic and often progressive diseases associated with a dysregulated or overactive immune system.

Asthma is the most common chronic disease among children and also affects millions of adults. Some 235 million people worldwide suffer from this disease.

COPD is a highly prevalent condition and a major cause of morbidity and mortality worldwide. As the disease progresses, patients with COPD may become prone to frequent exacerbations resulting in patient anxiety, worsening health status, lung function decline and increase in mortality rate. These episodes of worsening respiratory function lead to increases in health care utilization, hospital admissions and costs. Worse, frequent exacerbations are associated with a faster decline in lung function, thereby shortening life expectancy.

In addition to COPD and Asthma, other allergic and/or inflammatory disorders of lung include diseases such as Cystic Fibrosis and Idiopathic pulmonary fibrosis (IPF).

According to the recommendations of Global Initiative for Chronic Obstructive Lung Disease (GOLD), the first line therapy for COPD are long acting β-agonists, long acting muscarinic antagonist and inhalation corticosteroids. However, these drugs reduce the symptoms and exacerbations associated with the disease rather than targeting its molecular and cellular basis. Accordingly, there is still a need for further improvement in COPD therapy.

Roflumilast (Daliresp®), a PDE4 inhibitor, is approved as an oral therapy in the U.S. to reduce the risk of COPD exacerbations in patients with severe COPD associated with chronic bronchitis and a history of exacerbations.

In April 2010, the Pulmonary-Allergy Drugs Advisory Committee (PADAC) to the FDA voted 10 to 5 against approving roflumilast due to modest benefit and potential for adverse events. In March 2011, the FDA approved roflumilast with a narrower indication than had originally been pursued (namely, the treatment to reduce the risk of COPD exacerbations in patients with severe COPD associated with chronic bronchitis and a history of exacerbations). Roflumilast has been reported to have dose dependent toxicity, which limits the use of roflumilast at higher doses. The table below shows adverse events (AEs) that occurred in at least 2% of those receiving roflumilast and greater than placebo.

| AEs | Roflumilast (n = 4438) | Placebo (n = 4192) |
| --- | --- | --- |
| Diarrhoea | 420 (9.5) | 113 (2.7) |
| Weight loss | 331 (7.5) | 89 (2.1) |
| Nausea | 209 (4.7) | 60 (1.4) |
| Headache | 195 (4.4) | 87 (2.1) |
| Back pain | 142 (3.2) | 92 (2.2) |
| Influenza | 124 (2.8) | 112 (2.7) |
| Insomnia | 105 (2.4) | 41 (1.0) |
| Dizziness | 92 (2.1) | 45 (1.1) |
| Decreased appetite | 91 (2.1) | 15 (0.4) |

Data obtained from the FDA label for Dalresp® (roflumilast) Aug. 13, 2013

R. W. Chapman et al., *European Journal of Pharmacology*, 571, 215-221 (2007), report experiments involving administration of roflumilast by inhalation to Brown Norway rats in an attempt to improve its therapeutic index.

According to the label for Daliresp, roflumilast N-oxide is an active metabolite of roflumilast. International Publication Nos. WO 2001/90076 and WO 2011/163469, both of which are hereby incorporated by reference, disclose the preparation and certain uses of roflumilast N-oxide. Additional efficacy, preclinical and clinical information for roflumilast and roflumilast N-oxide is provided in A. Hatzelmann et al., *Journal of Pharmacology and Experimental Therapeutics*, 297, 267-279, 2001; Center For Drug Evaluation And Research Pharmacology Review(s) on Roflumilast (Application Number: 022522Orig1s000) available online on the U.S. FDA website; D. S. Bundschuh et al., *Journal of Pharmacology and Experimental Therapeutics*, 297, 280-290, 2001; Rabe et al., *Br. J. Pharmacol.*, 16353-67, 2011; Zuzana Diamant et al., *Pulmonary Pharmacology & Therapeutics* 24, 4 (2011) 353; and S. Vollert et al., *Diabetologia*, 55, 2779-2788, 2012, each of which is hereby incorporated by reference.

Despite currently available intervention therapies, respiratory disorders such as asthma and COPD remain a disease class with a significant unmet medical need. More effective therapies with fewer adverse events are needed.

SUMMARY OF THE INVENTION

The present invention provides a method of treating an autoimmune, respiratory and/or inflammatory disease and/or condition by pulmonary administration (e.g., by inhalation), an effective amount of roflumilast N-oxide or a pharmaceutically acceptable salt thereof. Without being bound by any particular theory, the inventors theorize that pulmonary administration of roflumilast N-oxide will result in lower plasma levels of roflumilast N-oxide and roflumilast and therefore fewer side effects than oral delivery of roflumilast. Furthermore, pulmonary delivery of roflumilast N-oxide has a broader therapeutic window than oral delivery of roflumilast. This permits a lower dosage of drug to be administered and/or a longer drug regimen with fewer adverse events.

The disease or condition can be asthma, COPD, chronic obstructive bronchiolitis, chronic bronchitis, or allergic or non-allergic rhinitis. In a preferred embodiment, the disease or condition is asthma or COPD.

The roflumilast N-oxide (or pharmaceutically acceptable salt thereof) can be administered by inhalation in the form of a dry powder, solution or suspension. In one embodiment, the roflumilast N-oxide is administered as a dry powder. In another embodiment, the roflumilast N-oxide is administered as a solution or suspension. The roflumilast N-oxide may be administered, for example, using a metered dose inhaler (MDI) or a dry powder inhaler (DPI). Alternatively, the roflumilast N-oxide may be administered with a nebulizer (e.g., an ultrasonic nebulizer).

In one embodiment, the roflumilast N-oxide is administered as a single dose of about 5 µg to about 2000 µg. In another embodiment, the roflumilast N-oxide is administered as a single dose of about 20 µg to about 1200 µg. One or more doses of the roflumilast N-oxide may be administered a day.

In yet another embodiment, the roflumilast N-oxide is administered as a single dose of about 50 µg to about 1000 ug, such as a single dose of about 100 µg to about 800 µg, for example, as a single dose of about 100 µg, about 200 µg, about 400 µg or about 600 µg.

The present invention also relates to a pharmaceutical composition suitable for pulmonary administration (e.g., by inhalation) comprising roflumilast N-oxide and optionally one or more pharmaceutically acceptable carriers and/or excipients. The pharmaceutical composition may be used in the methods of treatment described herein, such as for the treatment of asthma or COPD.

The pharmaceutical composition may be in the form of an inhalable dry powder comprising roflumilast N-oxide as an active ingredient and optionally particles of a physiologically acceptable, pharmacologically-inert solid carrier. In one preferred embodiment, the roflumilast N-oxide particles are in micronized form.

Yet another embodiment is a pharmaceutical composition in the form of an aerosol suitable for pulmonary administration comprising roflumilast N-oxide or a pharmaceutically acceptable salt thereof as an active ingredient, a propellant, and optionally one or more co-solvents, pharmaceutically acceptable carriers and/or excipients.

Yet another embodiment is a pharmaceutical composition suitable for pulmonary administration comprising a suspension of particles of roflumilast N-oxide or a pharmaceutically acceptable salt thereof (e.g., micronized particles of roflumilast N-oxide) in a propellant.

Yet another embodiment is a metered dose inhaler (MDI) or a dry powder inhaler (DPI) comprising a pharmaceutical composition comprising roflumilast N-oxide.

In any of the methods or compositions described herein, the roflumilast N-oxide can have a particle size (for example, $d_{50}$ or $d_{90}$) of less than about 10 microns. In a preferred embodiment, the roflumilast N-oxide has a mass median diameter, $d_{50}$, or $d_{90}$ equal to or less than about 10 microns, preferably less than about 6 microns and more preferably from about 1 to about 6 microns. In yet another embodiment, the roflumilast N-oxide has a mass median particle size, $d_{50}$, or $d_{90}$ of less than about 10 microns (e.g., from about 0.1 to about 10 microns, such as about 0.5 to about 5 microns).

The roflumilast N-oxide may be in the form of an anhydrate, a solvate, a hydrate or a salt with a pharmacologically acceptable acid or base. In a further embodiment of any of the methods or compositions described herein, the roflumilast N-oxide may be in combination with a second active agent, such as one or more of leukotriene receptor antagonists including LTD4-antagonists, corticosteroids, H1 receptor antagonists, β2 adrenoceptor agonists, COX-2 selective inhibitors, statins, non-steroidal anti-inflammatory drugs (NSAIDs), M2 and/or M3 antagonists, betamimetics, additional PDE4-inhibitors, EGFR-inhibitors, CCR3-inhibitors, iNOS-inhibitors, SYK-inhibitors, glucocorticoids, δ2 agonists, p38 kinase inhibitors, NK1 receptor antagonists or any combination of any of the foregoing.

In a preferred embodiment of any of the methods or compositions described herein, the roflumilast N-oxide is in combination with a second active agent selected from long-acting β2 agonists (LABA), M3 antagonists, corticosteroids, and any combination thereof.

DETAILED DESCRIPTION OF THE INVENTION

Figure 1:
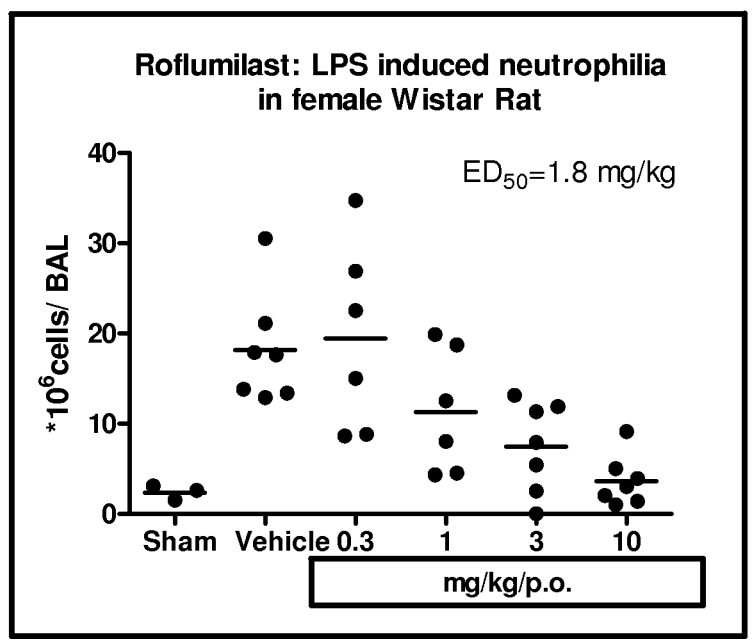
FIG. 1 is a scatter graph showing the effect of orally administered vehicle and roflumilast (RFL) (0.3, 1, 3, and 10 mg/kg) on the inhibition of LPS-induced neutrophilia in the bronchoalveolar lavage fluid (BALF) of female Wistar rats (Example 3B.A).

The methods of present invention allow for the treatment of respiratory and inflammatory diseases and conditions using a smaller amount of active compound and/or allow for the treatment of respiratory and inflammatory diseases and conditions for a longer period of time in a more efficient manner. The methods of present invention also allow for lower systemic side effects of roflumilast or roflumilast N-oxide than would have been expected upon oral administration of roflumilast N-oxide.

Roflumilast N-oxide has the formula:

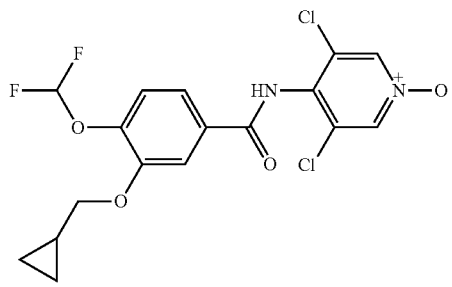

The roflumilast N-oxide may be in the form of a pharmaceutically acceptable salt. Suitable pharmaceutically acceptable salts include, but are not limited to, salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; salts of chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI and $(Me)_2SO_4$; salts of non-natural amino acids such as D-isomers or substituted amino acids; salts of guanidine; and salts of substituted guanidine wherein the substituent's are selected from nitro, amino, alkyl, alkenyl, alkynyl, ammonium or substituted ammonium salts and aluminum salts. Suitable salts may also include acid addition salts where appropriate, such as sulphates, nitrates, phosphates, perchlorates, borates, hydrohalides, acetates, tartrates, maleates, citrates, fumarates, succinates, palmoates, methane sulphonates, benzoates, salicylates, benzenesulfonates, ascorbates, glycerophosphates, and ketoglutarates.

When ranges are used herein for physical properties, such as molecular weight, or chemical properties such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The term "effective amount" or "therapeutically effective amount" refers to that amount of roflumilast N-oxide described herein that is sufficient to effect the intended application including, but not limited to, disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular method of administration of roflumilast N-oxide by inhalation chosen (e.g., by nebulization, aerosol for inhalation or dry powder for inhalation), the dosing regimen to be followed, whether it is administered in combination with other compounds, timing of administration, the tissue to which it is administered, and the physical delivery system in which it is carried.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as used herein encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" as used herein refers to any animal, such as a mammal, for example a human. The methods and compositions described herein can be useful in both human therapeutics and veterinary applications. In some embodiments, the patient is a mammal, and in some embodiments, the patient is human. For veterinary purposes, the terms "subject" and "patient" include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and Roflumilast N-oxide according to the invention encompass conditions associated with reactions of the specific defense system as well as conditions associated with reactions of the non-specific defense system.

The methods of the present invention include methods for the treatment of conditions associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including, but not limited to, monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Allergic disease" as used herein refers to any symptoms, tissue damage, or loss of tissue function resulting from an allergy.

"Arthritic disease" as used herein refers to any disease that is characterized by inflammatory lesions of the joints attributable to a variety of etiologies.

The pharmaceutical compositions of the invention may include a corticosteroid. Similarly, the methods described herein may include co-treatment and/or co-administration with a corticosteroid. The rofumilast N-oxide and corticosteroid may be in the same composition or in separate compositions which are co-administered. Suitable corticosteroids include, but are not limited to, dexamethasone, fluticasone, fluticasone furoate, prednisolone, betamethasone, budesonide, mometasone, mometasone furoate, triamcinolone acetonide, ciclesonide, TPI-1020, beclomethasone, beclomethasone dipropionate, prednisone, deflazacort, hydrocortisone, QAE-397, flunisolide, and any combination thereof.

The pharmaceutical compositions of the invention may include a second component, such as one or more LABAs (long-acting $\beta_2$ agonists), M3 antagonists, corticosteroids, and any combination of any of the foregoing. Similarly, the methods described herein may include co-treatment and/or co-administration with such a second component. The rofumilast N-oxide and second component may be in the same composition or in separate compositions which are co-administered.

The present invention also provides a method for the prevention or treatment of any disease wherein the activity of PDE4 receptors is implicated and inhibition of PDE4 receptor activity is desired, which methods comprise administering to a patient in need thereof a therapeutically effective amount of Roflumilast N-oxide alone, or in combination with a second compactive agent selected from LABA (long-acting $\beta_2$ agonists), M3 antagonists and/or corticosteroids.

The diseases wherein the activity of PDE4 receptors and inhibition of PDE4 receptors are implicated include, e.g., diseases of the respiratory tract, characterized by airway obstruction, such as asthma and COPD.

The present invention is also directed to a device which may be a single- or multi-dose dry powder inhaler, a metered dose inhaler or a soft mist nebulizer comprising Roflumilast N-oxide.

The present invention is also directed to a kit comprising a pharmaceutical composition of Roflumilast N oxide, alone or in combination with an additional active ingredient, in admixture with one or more pharmaceutically acceptable carriers and/or excipients, and a device which may be a single- or multi-dose dry powder inhaler, a metered dose inhaler or a soft mist nebulizer.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-I, IL-3 and tumor necrosis factor-alpha (TNF-$\alpha$). It also leads to an airway smooth muscle relaxation and a decrease in oedema.

PDE-4 inhibitors, such as roflumilast N-oxide, exhibit an in vitro inhibitory activity toward the PDE4 enzyme in the nM range and exhibit a remarkable activity in the lungs upon intratracheal administration in an animal model of COPD. They may also exhibit sustained pulmonary levels in the lungs, being undetectable in plasma, which is an index of a short systemic action.

For the treatment of the diseases of the respiratory tract as provided herein, roflumilast N-oxide is administered by inhalation. Inhalable preparations include, for example, inhalable powders, propellant-containing metering aerosols and propellant-free inhalable formulations.

For administration as a dry powder, a known single- or multi-dose inhalers may be utilized. The dry powder may be filled in gelatine, plastic or other capsules, cartridges or blister packs or in a reservoir. A diluent or carrier, generally chemically inert to Roflumilast N-oxide, e.g., lactose or any other additive suitable for improving the respirable fraction may be added to the powdered compounds of the invention.

Inhalation aerosols containing propellant gas such as hydrofluoroalkanes may contain the rofumilast N-oxide either in solution or in dispersed form. The propellant-driven formulations may also contain other ingredients such as co-solvents, stabilizers and optionally other excipients.

The propellant-free inhalable formulations comprising roflumilast N-oxide may be in form of solutions or suspensions in an aqueous, alcoholic or hydroalcoholic medium and they may be delivered by known jet or ultrasonic nebulizers or by soft-mist nebulizers such as Respimat®.

Roflumilast N-oxide may be administered as the sole active agent or in combination with one or more other pharmaceutical active ingredients including those currently used in the treatment of respiratory disorders, such as for example, but not limited to, $\beta_2$-agonists, corticosteroids and M3 antagonists.

The dosages of roflumilast N-oxide may depend upon a variety of factors including the particular disease to be treated, the severity of the symptoms, the frequency of the dosage interval, rofulumilast N-oxide utilized, the efficacy, toxicology profile, and pharmacokinetic profile of rofulumilast N-oxide.

Advantageously, rofulumilast N-oxide may be administered by the inhalation route. The dosage of roflumilast N-oxide is preferably between about 0.01 and about 20 mg/day, such as between about 0.1 and about 10 mg/day. More preferably, the dosage is between about 0.1 and about 5 mg/day.

Preferably, rofulumilast N-oxide alone or combined with other active ingredients may be administered for the prevention, treatment, inhibition, or suppression of any obstructive respiratory disease such as asthma, chronic bronchitis and chronic obstructive pulmonary disease (COPD).

Rofulumilast N-oxide may be administered for the prevention and/or treatment of any disease wherein the activity of PDE4 enzyme is implicated and inhibition of PDE4 enzyme activity is desired, or a disease state which is mediated by PDE4 activity (for instance a disease state in which PDE4 is overexpressed or overactive).

Examples of such diseases include, but are not limited, allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, idiopathic pulmonary fibrosis (IPF) arterial restenosis, atherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, itching in the anogenital area, alopecia areata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, and autoimmune diseases.

Examples of such diseases also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Pharmaceutical Compositions

One aspect of the present invention provides a pharmaceutical formulation comprising roflumilast N-oxide in the form of an inhalable dry powder wherein the formulation comprises micronized particles of a roflumilast N-oxide as an active ingredient, and particles of a physiologically acceptable pharmacologically-inert solid carrier. Prior to the present invention, it was not known that roflumilast N-oxide could be prepared as micronized particles suitable for inhalation.

According to another aspect, the present invention provides a dry powder inhaler comprising an inhalable dry powder of any embodiment described herein.

A further aspect of the present invention refers to an inhalable dry powder of the present invention for use for the prevention and/or treatment of a disease where the PDE4 enzyme is implicated and inhibition of PDE4 enzyme activity is desired, or a disease state which is mediated by PDE4 activity, and in particular use for the prevention and/or treatment of an inflammatory or obstructive airways disease such as asthma or chronic obstructive pulmonary disease (COPD).

Another aspect of the present invention refers to a method of preventing, treating, inhibiting, or suppressing an inflammatory or obstructive airways disease such as asthma or chronic obstructive pulmonary disease (COPD), the method comprising administration by inhalation of a therapeutically effective amount of an inhalable dry powder according to any embodiment described herein.

Another aspect of the present invention is directed to a package comprising an inhalable dry powder formulation according to any embodiment described herein and a dry powder inhaler.

By "single therapeutically effective dose" it is meant the quantity of active ingredient administered at one time by inhalation upon actuation of the inhaler. The "single therapeutically effective dose" may be delivered in one or more actuations, preferably one actuation (shot) of the inhaler. For "actuation" it is meant the release of active ingredient from the device by a single activation (e.g. mechanical or by breath).

In general terms, the particle size of particles is quantified by measuring a characteristic equivalent sphere diameter, known as volume diameter, by laser diffraction. The particle size can also be quantified by measuring the mass diameter by means of a suitable known instrument such as, for instance, a sieve analyzer.

The volume diameter (VD) is related to the mass diameter (MD) by the density of the particles (assuming a size independent density for the particles).

The particle size may be expressed in terms of mass diameter (MD) and the particle size distribution is expressed in terms of: i) the mass median diameter (MMD) which corresponds to the diameter of 50 percent by weight or volume respectively, of the particles, and ii) the MD in micron of 10% and 90% of the particles, respectively. The terms MMD and mean particle size are used interchangeably. In particle size measurements, $d_{90}$, $d_{50}$ and $d_{10}$ respectively mean that 90%, 50% and 10% of the material is less than the micron size specified.

Laser diffraction measurement of particle size can use a dry method (wherein a suspension of the compound/salt in an airflow crosses the laser beam) or a wet method (wherein a suspension of the compound/salt in a liquid dispersing medium, such as isooctane (e.g. if compound is soluble in isooctane) or 0.1% Tween 80 in water, crosses the laser beam). With laser diffraction, particle size may be measured, for example, with a Malvern Mastersizer or Sympatec apparatus. For example, particle size measurement and/or analysis by laser diffraction can use any or all of (preferably all of) the following: a Malvern Mastersizer longbed version, a dispersing medium of 0.1% Tween 80 in water, a stir rate of ca. 1500 rpm, ca. 3 mins sonification prior to final dispersion and analysis, a 300 RF (Reverse Fourier) lens, and/or the Fraunhofer calculation with Malvern software. Unless specified otherwise, all d50 and d90 measurements are measured by laser diffraction using a wet method.

The expression "respirable fraction" refers to an index of the percentage of active particles which would reach the deep lungs in a patient. The respirable fraction, also termed fine particle fraction, is evaluated using a suitable in vitro apparatus such as Multistage Cascade Impactor or Multi Stage Liquid Impinger (MLSI) according to procedures reported in common Pharmacopeias. It is calculated by the ratio between the delivered dose and the fine particle mass (formerly fine particle dose). A respirable fraction higher than 30% is an index of good inhalatory performance.

The delivered dose is calculated from the cumulative deposition in the apparatus, while the fine particle mass is calculated from the deposition on Stages 3 (S3) to filter (AF) corresponding to particles <4.7 microns. The expression "accurate therapeutically active dose of the active ingredient" refers to a formulation wherein the variation between the mean delivered daily dose and the mean emitted dose is equal to or less than 15%, preferably less than 10%.

In one aspect, the compositions of the invention are pharmaceutical formulations in the form of inhalable dry powder comprising micronized particles of a Roflumilast N-oxide and particles of a physiologically acceptable pharmacologically-inert solid carrier.

The compositions according to the invention comprise the active ingredient in an amount such that, in case of administration by inhalation from inhalers, the therapeutically effective single dose (hereinafter the single dose) of a roflumilast N-oxide comprises between about 5 μg and about 2000 μg, such as between about 20 μg and about 1200 μg, e.g., between about 50 μg and about 1000 μg, between about 100 μg and about 800 μg or between about 100 μg, and about 600 μg.

According to a preferred embodiment, the single dose may be between about 100 and about 300 μg, while according to another preferred embodiment; the single dose may be comprised between about 200 and about 800 μg, more preferably between about 300 ug and about 600 μg. In other embodiments, the single dose may be about 100 μg, about 200 μg, about 400 μg or about 600 μg.

The single dose will depend on the kind and the severity of the disease and the conditions (weight, sex, age) of the patient and shall be administered one or more times a day, preferably once or twice a day.

The daily dose at which the pharmaceutical composition comprising a Roflumilast N-oxide shall be comprised between about 100 μg and about 2000 μg, preferably between about 200 μg and about 1000 μg, more preferably between about 200 μg and about 800 μg and more preferably between about 100 μg and about 600 μg.

In one embodiment, the daily dose may be reached by a single or double administration.

In another embodiment, the daily dose may be reached by a single administration and delivered in one actuation of the inhaler.

In another embodiment, the daily dose may be reached by a single administration and delivered in more than one actuation of the inhaler, preferably two actuations In another embodiment, the daily dose may be reached by a double administration and delivered in one actuation of the inhaler.

In another embodiment, the daily dose may be reached by a double administration and delivered in more than one actuation of the inhaler, preferably two actuations.

The particles of Roflumilast N-oxide in the formulations according to the present invention are preferably in a finely divided (micronized) form, i.e. their mass median diameter should generally be equal to or less than about 10 microns, preferably less than about 6 microns, more preferably comprised between about 1 and about 6 microns.

The active ingredient may be produced in the desired particle size using known methods, e.g., by milling, direct precipitation, spray-drying, freeze-drying or supercritical fluids.

The carrier particles may be made of any physiologically acceptable pharmacologically-inert material or combination of materials suitable for inhalatory use.

For example, the carrier particles may be selected from sugar alcohols; polyols, for example sorbitol, mannitol and xylitol, and crystalline sugars, including monosaccharides and disaccharides; inorganic salts such as sodium chloride and calcium carbonate; organic salts such as sodium lactate; and other organic compounds such as urea, polysaccharides, for example starch and its derivatives; oligosaccharides, for example cyclodextrins and dextrins.

Advantageously the carrier particles are made of a crystalline sugar, for example, a monosaccharide such as glucose or arabinose, or a disaccharide such as maltose, saccharose, dextrose or lactose.

The formulations described herein may be prepared according to known methods. Generally the process comprises the steps of:

i) micronising together the active ingredient and the carrier; and ii) subjecting the resulting co-micronized mixture to agglomeration and spheronisation.

Alternatively, the process comprises the following steps:

i) micronising separately the active ingredient and the carrier; ii) mixing the micronized components; and iii) subjecting the resulting mixture to agglomeration and spheronisation.

When a formulation of the invention is in form of an ordered mixture, it may advantageously comprise an additive material able to promote the release of the active particles from the carrier particles on actuation of the inhaler device, thereby improving the respirable fraction.

The additive material, which is preferably bound to the surface of the carrier coarse particles, is of a different material from the carrier particles.

The additive material may be an amino acid, preferably selected from leucine, isoleucine, lysine, valine, methionine, and phenylalanine. The additive may be a salt of a derivative of an amino acid, for example aspartame or acesulfame potassium.

Alternatively, the additive material may include or be one or more water soluble surface active materials, for example lecithin, in particular soya lecithin.

In a particular embodiment of the invention, the additive material may include or consist of one or more lubricant selected from the group consisting of stearic acid and salts thereof such as magnesium stearate, sodium lauryl sulphate, sodium stearyl fumarate, stearyl alcohol, sucrose monopalmitate.

Other possible additive materials include talc, titanium dioxide, aluminium dioxide, and silicon dioxide.

Advantageously, the additive particles have a starting mean particle size or $d_{50}$ of less than about 35 microns. Preferably they have a mean particle size or $d_{50}$ of not more than 1 about 5 microns, more preferably not more than about 10 microns The optimum amount of additive material depends on the chemical composition and other properties of the additive material. In general, the amount of additive is not more than about 10% by weight, based on the total weight of the formulation. In certain embodiments, the amount of additive material is not more than about 5%, preferably not more than about 2%, not more than about 1% by weight or not more than about 0.5% based on the total weight of the formulation. In general, the amount of additive material is at least 0.01% by weight based on the total weight of the formulation.

The formulations of the invention in the form of ordered mixture may also comprise fine particles of a physiologically acceptable pharmacologically-inert material with a mass median diameter (MMD) equal to or less than about 15 micron, preferably equal to or less than about 10 microns, even more preferably equal to or less than about 6 microns.

The percentage of fine particles of physiologically acceptable pharmacologically-inert material is advantageously comprised between about 0.1 and about 40% of the total amount of the formulation.

Preferably, the coarse particles and the fine particles are constituted of the same physiologically acceptable pharmacologically-inert material.

A formulation in the form of an ordered mixture according to the invention may be prepared according to known methods. Suitable methods may comprise the step of mixing together the carrier coarse particles, the optional fine carrier particles and the additive particles, and finally adding the finely divided Roflumilast N-Oxide to the resulting mixture. A preferred formulation according to the invention may be prepared according to the methods reported in International Publication No. WO 2001/78693.

The presence of the additive material embedded in the microparticles may be detected according to known methods, for instance, by electron scanning microscope coupled to microcalorimetry.

The formulations of the invention may further comprise other therapeutic agents useful for the prevention and/or treatment of a respiratory disease, e.g. β2-agonists such as salbutamol, salmeterol, and vilanterol, corticosteroids such as fluticasone propionate or furoate, flunisolide, mometasone furoate, rofleponide and ciclesonide, anticholinergic or antimuscarinic agents such as ipratropium bromide, oxytropium bromide, tiotropium bromide, oxybutynin, and combinations thereof.

The dry powder formulations described herein may be used in all customary dry powder inhalers, such as unit dose or multidose inhalers.

For example, the formulation of the invention may be filled in hard gelatine capsules, in turn loaded in a unit dose inhaler such as the Aerolizer™. Alternative, the formulation as a powder may be filled in a multidose inhaler comprising a powder reservoir such as that described in International Publication No. WO 2004/012801.

The invention also relates to any one of the formulations described before, for use as a medicament.

In one aspect, the present invention provides a pharmaceutical formulation suitable for aerosol administration by a Pressurized Metered Dose Inhaler (pMDI), (hereinafter referred to as a pMDI formulation, comprising roflumilast N-oxide and a propellant.

In a particular embodiment, the pMDI formulation may be in form of suspension of particles of a micronized roflumilast N-oxide in a propellant, so as to permit inhalation of the active ingredient into the lungs upon administration of the aerosol formulation.

Advantageously the particles of the active ingredient shall have a mass median diameter (MMD) of less than about 10 microns, preferably in the range of about 1 to about 10 microns, more preferably between about 1 and about 6 microns.

Any pressure-liquefied propellant may be used, preferably a hydrofluoroalkane (HFA) propellant. Suitable examples of HFA propellants include, but are not limited to, 1,1,1,2-tetrafluoroethane (HFA 134a), 1,1,1,2,3,3,3-heptafluoropropane (HFA227) and mixtures thereof.

In certain embodiments the propellant may include HFA 134a, while in other embodiments, the propellant may include HFA 227, or a mixture thereof in any ratio.

In a particular embodiment the suspension pMDI formulations comprise a surfactant, which may also act as a valve lubricant.

Suitable surfactants are known in the art and include, for example, sorbitan esters such as sorbitan trioleate, sorbitan monolaurate, sorbitan mono-oleate and their ethoxylated derivates such as polysorbate 20, polysorbate 80; ethylene oxide/propylene oxide co-polymers and other agents such as natural or synthetic lecithin, oleic acid, polyvinylpyrrolidone (PVP), preferably PVP (K25) and polyvinyl alcohol, olive oil, glyceryl monolaurate, corn oil, cotton seed oil or sunflower seed oil, isopropyl myristate, oleyl alcohol, polyoxyethylene (20) sorbitan monolaurate, polyoxy ethylene (20) sorbitan mono-oleate, oleyl polyoxyethylene (2) ether, stearyl polyoxyethylene (2) ether, lauryl polyoxyethylene (4) ether, block co-polymers of oxyethylene and oxypropylene, diethylene glycol dioleate, tetrahydro fur fury l oleate, ethyl oleate, glyceryl mono-oleate, glyceryl monostearate, glyceryl monoricinoleate, cetyl alcohol, stearyl alcohol, cetyl pyridinium chloride, ethylene oxide/propylene oxide co-polymer and ethoxylated alcohols such as polyethylene glycol (PEG) 300-1000, diethylene glycol monoethyl ether, Antarox, Brij, and any combination of the foregoing.

The amount of surfactant, which may be present in the pMDI formulation according to the invention, is usually in the range of about 0.001 to about 3.0% (w/w), preferably between about 0.005 and about 1.0% (w/w).

Optionally, the pMDI formulation may contain a co-solvent. Suitable co-solvents include, but are not limited to, polar compounds that contain one or more hydroxyl groups or other polar groups. For example, suitable co-solvents include an alcohol, such as ethanol, preferably anhydrous ethanol, isopropanol; a glycol such as propylene glycol, polyethylene glycol, polypropylene glycol or glycerol; a glycol ether; and a polyoxy ethylene alcohol, or any combination thereof.

In one embodiment, the co-solvent is anhydrous ethanol. In a preferred embodiment, the anhydrous ethanol is used in a concentration lower than about 20% (w/w), preferably below about 15%, more preferably between about 1% and about 5% (w/w), most preferably about 1% (w/w) or about 5% (w/w).

In other embodiments, the pMDI formulations according to the invention may additionally include additional excipients. Examples of additional excipients include sugars such as lactose, amino acids such as alanine, betaine, cysteine, and/or antioxidants such as ascorbic acid, citric acid, sodium edetate, editic acid, tocopherols, butylhydroxytoluene, butylhydroxyanisol and ascorbyl palmitate.

The weight ratio of the drug to the excipient is generally in the range from about 1:0.1 to about 1:100.

The pharmaceutical pMDI formulation of the invention may contain Roflumilast N-oxide in an amount between about 0.02 and about 0.7% w/w, preferably between about 0.05 and about 0.5%, a co-solvent in an amount between about 1 and about 5% w/w, and one or more surfactants in an amount between about 0.001% and about 3% w/w.

To prepare the suspension pMDI formulation according to the invention, Roflumilast N-oxide is micronized by methods known in the art, to prepare the active substance in the form of particles having a typical particle size suitable for inhalation, such as a $d_{50}$ or $d_{90}$ less than equal to 5 µm and more preferably such as less than equal to 3 µm.

According to another aspect, the present invention provides a pMDI comprising a canister filled with a pharmaceutical formulation of the present invention and a metering valve for delivering a daily therapeutically effective dose of the active ingredient.

The pMDI formulation of the invention is filled into pMDIs. The pMDIs comprise a canister fitted with a metering valve. Actuation of the metering valve allows a small portion of the spray product to be released to a subject.

In one embodiment, the formulation is actuated by a metering valve capable of delivering a volume of between about 25 µl and about 100 µl, Advantageously, the MDI device filled with the formulation may be equipped with a dose counter.

Conventional bulk manufacturing methods and known machinery may be employed for the preparation of large scale batches for the commercial production of filled canisters.

For example, the pMDI suspension formulations according to the invention may be prepared by adding the active ingredient to a chilled propellant or optionally a pre-mixed blend of propellant and optionally further excipients and, then dispersing the resulting suspension using a suitable mixer. After homogenization the suspension can be filled into the MDI canister which is closed by crimping a metering valve on the canister.

Alternatively, the active ingredient and optionally further excipients can be added to a vessel. The liquefied propellant is then introduced into the vessel under pressure and the active ingredient is dispersed and homogenized using a suitable mixer and homogenizer. After homogenization the bulk formulation can be transferred into the individual MDI canisters by using valve to valve transfer methods.

Alternatively, the co-solvent, if present, is introduced into a vessel at room pressure. The active ingredient and optional further excipients are added and homogenised using a suitable homogenizer. The ethanolic suspension is kept under stirring. The ethanolic bulk is then dosed into the open canister. The valve is placed onto the can and crimped. Finally, the canister is pressure-filled with the final solution formulation through the valve.

The pMDI formulations according to the invention, depending on volume of the metering valve to be used, may comprise from about 0.1 mg to about 50 mg of Roflumilast N-oxide per ml, preferably from about 0.5 mg to about 25 mg of Roflumilast N-oxide per ml.

The pMDI formulations in the form of suspensions comprising particles of a micronized Roflumilast N-oxide and a propellant, comprise the active ingredient in an amount such that, in the case of administration by inhalation from inhalers, the daily therapeutically effective dose (hereinafter the daily dose) of Roflumilast N-oxide is between about 5 µg and about 2000 µg, preferably between about 20 µg and about 1500 µg, even more preferably between about 50 µg and about 1000 µg, even more preferably between about 60 µg and about 800 µg, even more preferably between about 200 µg and about 600 µg.

According to a preferred embodiment, the single dose is between about 100 µg and about 300 µg. According to another preferred embodiment, the single dose is between about 200 µg and about 800 µg, more preferably between about 300 µg and about 600 µg.

In further embodiments, the single dose may be about 100 µg, about 200 µg, about 400 µg or about 600 µg.

The single dose will depend on the kind and the severity of the disease and the conditions (weight, sex, age) of the patient and will be administered one or more times a day, preferably once a day.

The daily dose may be delivered in one or two or more actuations (shots) of the inhaler wherein the pharmaceutical composition is contained. For example, a 400 µg daily dose may be administered in one shot of 400 µg or as two shots of 200 µg dose.

In another aspect, Roflumilast N-oxide may be dissolved or suspended to give a nebulised aqueous solution or suspension (herein called a nebulised formulation), available either as for a single dose or multi-dose vials formulation.

The nebulised formulation may have the pH and/or tonicity adjusted with suitable buffers and/or isotonic agents, and optionally, it may also comprise stabilizing and/or preserving agents.

The present invention also provides a single dose or multidose vial filled with a nebulised formulation as described herein for delivering a daily therapeutically dose of the active ingredient by a nebulizer.

A liquid, propellant-free pharmaceutical formulation in the form of a ready-to-use preparation for administration by nebulisation of the invention, comprises Roflumilast N-oxide in an amount such that the daily dose is between about 35 µg and about 7000 µg, preferably between about 70 µg and about 3500 µg, even more preferably between about 175 µg and about 2800 µg, even more preferably between about 280 µg and about 2100 µg, even more preferably between about 350 µg and about 1750 µg.

According to a preferred embodiment, the single dose may be comprised between about 350 µg and about 700 µg, while according to another preferred embodiment, the single dose may be comprised between about 700 µg and about 1400 µg.

In further embodiments, the single dose may be about 350 µg, about 700 µg or 1400 µg.

The formulation is preferably used as a ready-to-use formulation.

In another embodiment, the nebulised formulation may also be in a lyophilised form in unitary doses for the reconstitution in a solution. In this embodiment, a single dose of a lyophilised preparation may be reconstituted before use.

These nebulised formulations may also be distributed in suitable containers such as multidose vials or, preferably, single dose vials for single dosage administration. Said single-dose vials may be pre-sterilised or, preferably, may be aseptically filled using "blow, fill and seal" technology (see http://www.brevettiangela.com). The filling is preferably carried out under inert atmosphere.

Solution formulations can be advantageously sterilized by filtration.

The single-dose vials are preferably 2 ml volume. For suspension formulations, the sterilization process is carried out through known techniques.

These formulations are intended for administration using suitable nebulizing apparatus such as jet nebulizers, ultrasonic nebulizers, mesh-vibrating nebulizers, soft-mist nebulizers such as Respimat® or others.

The invention is also directed to a kit comprising a nebulised formulation as described herein filled in vials for single dosage administration and a nebulizer.

All the pMDI and nebulized formulations of the present invention may further comprise other therapeutic agents, such as those used in the treatment of respiratory disorders, e.g. corticosteroids such as triamcinolone acetonide, fluticasone propionate, fluticasone furoate, flunisolide, mometasone furoate, rofleponide and ciclesonide; anticholinergic or antimuscarinic agents such as ipratropium bromide, oxytropium bromide, glycopyrronium bromide and tiotropium bromide; long-acting $\beta_2$ agonists such as vilanterol, indacaterol, milveterol, salbutamol, levalbuterol, terbutaline, AZD-3199, BI-1744-CL, LAS-100977, bambuterol, isoproterenol, procaterol, clenbuterol, reproterol, fenoterol and ASF-1020 and salts thereof.

The invention also relates to any one of the formulations described before, for use as a medicament.

In a further aspect, the present invention comprises any one of the formulations described before, for use in the prevention and/or treatment of an inflammatory or obstructive airways disease such as asthma or chronic obstructive pulmonary disease (COPD).

In a further aspect, the present invention comprises the use of any one of the formulations described before, in the prevention and/or treatment of an inflammatory or obstructive airways disease such as asthma or chronic obstructive pulmonary disease (COPD).

In a still further aspect, the present invention comprises a method of preventing and/or treating an inflammatory or obstructive airways disease such as asthma or chronic obstructive pulmonary disease (COPD), which comprises administration by inhalation of an effective amount of one of the formulations described before.

Administration of all the formulations of the invention may be indicated for the prevention and/or treatment of mild, moderate or severe acute or chronic symptoms or for prophylactic treatment of respiratory diseases such as asthma and chronic obstructive pulmonary disease (COPD). Other respiratory disorders characterized by obstruction of the peripheral airways as a result of inflammation and presence of mucus such as chronic obstructive bronchiolitis and chronic bronchitis may also benefit by this kind of formulation.

A further embodiment of the present invention relates to a pharmaceutical composition according to the present invention for use in the treatment of respiratory and inflammatory diseases and conditions, particularly wherein the respiratory and inflammatory diseases or conditions are selected from asthma, allergic and non-allergic rhinitis and COPD.

In a further embodiment of any of the methods or compositions described herein, the Roflumilast N-oxide is in combination with a second active agent, selected from, for example, leukotriene receptor antagonists including LTD4-antagonists, corticosteroids, H1 receptor antagonists, β2 adrenoceptor agonists, COX-2 selective inhibitors, statins, non-steroidal anti-inflammatory drugs ("NSAIDs"), M2 and/or M3 antagonists, betamimetics, additional PDE4-inhibitors, EGFR-inhibitors, CCR3-inhibitors, iNOS-inhibitors, SYK-inhibitors, glucocorticoids, δ2 agonists, p38 kinase inhibitors, NK1 receptor antagonists and any combination thereof.

Suitable β2-agonists for use in the present invention include, but are not limited to, arformoterol, bambuterol, bitolterol, broxaterol, carbuterol, clenbuterol, dopexamine, fenoterol, formoterol, hexoprenaline, ibuterol, Isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, GSK-597901, GSK-159797, GSK-678007, GSK-642444, GSK-159802, HOKU-81, (−)-2-[7(S)-[2(R)-Hydroxy-2-(4-hydroxyphenyl) ethylamino]-5,6,7,8-tetrahydro-2-naphthyloxy]-N,N-dimethylacetamide hydrochloride monohydrate, carmoterol, QAB-149 and 5-[2-(5,6-diethylindan-2-ylamino)-1-hydroxyethyl]-8-hydroxy-1H-quinolin-2-one, 4-hydroxy-7-[2-{[2-{[3-(2-phenylethoxy)propyl]sulfonyl}ethyl]amino}ethyl]-2(3H)-benzothiazolone, 1-(1-fluoro-4-hydroxyphenyl)-2-[4-(1-benzimidazolyl)-2-methyl-2-butylamino]ethanol, 1-[3-(4-methoxybenzylamino)-4-hydroxyphenyl]-2-[4(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert-butylamino)ethanol, 1-(4-ethoxycarbonylamino-3-cyano-5-fluorophenyl)-2-(tert-butylamino)ethanol, and combinations thereof, each of which is optionally in the form of a racemate, enantiomer, diastereomer, or mixtures thereof, and also optionally in the form of a pharmacologically-compatible acid addition salt.

Suitable corticosteroids and glucocorticoids for use in the present invention include, but are not limited to, prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate, hydrocortisone probutate and combinations thereof.

Suitable LTD4 antagonists for use in the present invention include, but are not limited to, tomelukast, ibudilast, pobilukast, pranlukast hydrate, zafirlukast, ritolukast, verlukast, sulukast, cinalukast, iralukast sodium, montelukast sodium, 4-[4-[3-(4-Acetyl-3-hydroxy-2-propylphenoxy)propylsulfonyl]phenyl]-4-oxobutyric acid, [[5-[[3-(4-Acetyl-3-hydroxy-2-propylphenoxy)propyl]thio]-1,3,4-thiadiazol-2-yl]thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl]phenyl]-8-(N,N-dimethylcarbamoyl)-4,6-dithiaoctanoic acid sodium salt; 3-[1-[3-[2-(7-Chloroquinolin-2-yl)vinyl]phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d]pyrimidin-9(1H-one, 4-[6-Acetyl-3-[3-(4-acetyl-3-hydroxy-2-propylphenylthio)propoxy]-2-propylphenoxy]butyric acid, (R)-3-Methoxy-4-[1-methyl-5-[N-(2-methyl-4,4,4-trifluorobutyl)carbamoyl]indol-3-ylmethyl]-N-(2-methylphenylsulfonyl)benzamide, (R)-3-[2-Methoxy-4-[N-(2-methylphenylsulfonyl)carbamoyl]benzyl]-1-methyl-N-(4,4,4-trifluoro-2-methylbutyl)indole-5-carboxamide, (+)-4(S)-(4-Carboxyphenylthio)-7-[4-(4-phenoxybutoxy)phenyl]-5(Z)-heptenoic acid, compounds International Application No. PCT/EP03/12581, and combinations thereof.

Suitable inhibitors of egfr-kinase for use in the present invention include, but are not limited to, palifermin, cetuximab, gefitinib, repifermin, erlotinib hydrochloride, canertinib dihydrochloride, lapatinib, N-[4-(3-Chloro-4-fluorophenylamino)-3-cyano-7-ethoxyquinolin-6-yl]-4-(dimethylamino)-2(E)-butenamide, and combinations thereof.

Suitable p38 kinase inhibitors for use in the present invention include, but are not limited to, chlormethiazole edisylate, doramapimod, 5-(2,6-Dichlorophenyl)-2-(2,4-difluorophenylsulfanyl)-6H-pyrimido[3,4-b]pyridazin-6-one, 4-Acetamido-N-(tert-butyl)benzamide, SCIO-469 (described in Abst. of Clin. Pharmacol. Ther., 75(2), 2004, PII-7 and VX-702 (described in Circulation, 108 (17, Suppl. 4), Abst 882, 2003), and combinations thereof.

Suitable NK1-receptor antagonists for use in the present invention include, but are not limited to, nolpitantium besilate, dapitant, lanepitant, vofopitant hydrochloride, aprepitant, eziopitant, N-[3-(2-Pentylphenyl)propionyl]-threonyl-N-methyl-2,3-dehydrotyrosyl-leucyl-D-phenylalanyl-allo-threonyl-asparaginyl-serine C-1.7-O-3.1 lactone, 1-Methylindol-3-ylcarbonyl-[4(R)-hydroxyl-L-prolyl-(3-(2-naphthyl)]-L-alanine N-benzyl-N-methylamide, (+)-(2S,3S)-3-[2-Methoxy-5-(trifluoromethoxy)benzylamino]-2-phenylpiperidine, (2R,4S)—N-[1-[3,5-Bis(trifluoromethyl)benzoyl]-2-(4-chlorobenzyl)piperidin-4-yl]quinoline-4-carboxamide, 3-[2(R)-[1(R)-[3,5-Bis(trifluoromethyl)phenyl]ethoxy]3(S)-(4-fluorophenyl)morpholin-4-ylmethyl]-5-oxo-4,5-dihydro-1H-1,2,4-triazole-1-phosphinic acid bis(N-methyl-D-glucamine) salt; [3-(2(R)-[1(R)-[3,5-bis(trifluoromethyl)phenyl]ethoxy]-3(S)-(4-fluorophenyl)-4-morpholinylmethyl]-2,5-dihydro-5-oxo-1H-1,2,4-triazol-1-yl]phosphonic acid 1-deoxy-1-(methylamino)-D-glucitol (1:2) salt, 1'-[2-[2(R)-(3,4-Dichlorophenyl)-4-(3,4,5-trimethoxybenzoyl)morpholin-2-yl]ethyl]spiro[benzo[c]thiophen-1(3H)-4'-piperidine] 2(S)-oxide hydrochloride and the compound CS-003 (described in Eur. Respir. J., 22(Suppl. 45): Abst P2664, 2003) and combinations thereof.

Suitable NSAIDs for use in the present invention include, but are not limited to, Aceclofenac, acemetacin, acetylsalicylic acid, alclofenac, alminoprofen, amfenac, Ampiroxicam Antolmetinguacil, Anirolac, antrafenine, azapropazone, benorylate, Bermoprofen, bindarit, bromfenac, bucloxic acid, Bucolom, Bufexamac, Bumadizon, butibufen, Butixirat, Carbasalatcalcium, carprofen, choline magnesium trisalicylate, celecoxib, Cinmetacin, Cinnoxicam, clidanac Clobuzarit Deboxamet, dexibuprofen, Dexketoprofen, diclofenac, diflunisal, droxicam, Eltenac Enfenaminsaure Etersalat, etodolac, etofenamate, etoricoxib Feclobuzon felbinac, fenbufen, fenclofenac, fenoprofen, fentiazac, Fepradinol Feprazon, Flobufen, floctafenine, flufenamic acid, flufenisal, Flunoxaprofen, flurbiprofen, Flurbiprofenaxetil, Furofenac, Furprofen, Glucametacin, ibufenac, ibuprofen, Indobufen, indomethacin, Indometacinfarnesil, indoprofen, Isoxepac, Isoxicam, ketoprofen, ketorolac, lobenzarit, Lonazolac, lornoxicam, Loxoprofen, lumiracoxib, meclofenamic, Meclofen, mefenamic acid, meloxicam, mesalazine, Miro Profen, Mofezolac, nabumetone, naproxen, niflumic acid, olsalazine, oxaprozin, Oxipinac, oxyphenbutazone, parecoxib, phenylbutazone, Pelubiprofen, Pimeprofen, Pirazolac, Priroxicam, pirprofen, Pranoprofen, Prifelon, Prinomod, Proglumetacin, Proquazon, Protizininsaure, rofecoxib, Romazarit, salicylamide, salicylic acid, Salmi Stein, Salnacedin, salsalate, sulindac, sudoxicam, suprofen, Talniflumate, tenidap, Tenosal, tenoxicam, tepoxalin, tiaprofenic acid, Taramid, Tilnoprofenarbamel, timegadine, Tinoridin, Tiopinac, tolfenamic acid, tolmetin, Ufenamat, valdecoxib, Ximoprofen, zaltoprofen, Zoliprofen and combinations thereof.

The combinations described herein may be used in the treatment of any disorder which is susceptible to amelioration by simultaneous, concomitant or sequential inhibition of phosphodiesterase 4 (PDE4). Thus, the present invention also includes methods of treatment of these disorders, as well as the use of the combinations of the invention in the manufacture of a medicament for the treatment of these disorders.

Preferred examples of such disorders are those respiratory diseases, wherein the use of bronchodilating agents is expected to have a beneficial effect, for example asthma, acute or chronic bronchitis, emphysema, or Chronic Obstructive Pulmonary Disease (COPD).

Micronization of Roflumilast N-Oxide

In one preferred embodiment, the roflumilast N-oxide to be administered by inhalation is micronized. Micronization can be performed by mechanical impact (e.g., by the use of mills, such as hammer mills, pin mills or bead milling) or by impact via fluid energy (e.g., by jet milling or the use of spiral jet mills or fluidized bed jet mills). Additional details on micronization and the micronization process are provided in a Spring 2005 Pharmaceutical Manufacturing and Packaging Sourcerarticle by J. M Larran, Journal of Pharmaceutical Processing, "Advances in Powder Micronization Technology in Pharmaceutical Industry by Hokosawa Micron Powder System;" Wikipedia entry on micronization; G. Gianola, "Micronization Systems—Innovative Equipment Design and Applications," presentation at Advances in Pharmaceutical Processing (Somerset, N.J., 2012) and R. Smith, "Micronization of Active Pharmaceutical Ingredients to Nanometer Scale," presentation at Advances in Pharmaceutical Processing (Somerset, N.J., 2012).

Provided below is an exemplary method used for micronization of roflumilast N-Oxide using an Alpine Spiral Jet Mill (HOSOKAWA). The process involved the following steps
15 gm of Roflumilast N-oxide was weighed.
Main knob for compressed air supply was opened.
Adjusted venture pressure at 6.0 bar and ring pressure at 0.5 bar.
Roflumilast N-oxide was added at a feed rate of ~200 mg/min manually through the hopper.
After completion of micronization, main air supply knob was turned off and micronized roflumilast N-oxide was collected
Yield: ~9.0 g (~60% yield). Particle Size Distribution (PSD) of $D_{90}$: 3.021 μm; $D_{50}$: 1.564 μm and $D_{10}$: 0.777 μm

EXAMPLES

The present invention is now further illustrated by means of the following non-limiting examples.

The experiments below show that roflumilast-N-oxide can be effectively delivered by inhalation at low doses to achieve an equal or better biological effect than that observed for roflumilast administered orally.

Example 1: Lung Microsome Stability of Roflumilast and Roflumilast N-oxide

Metabolic stability studies were conducted using rat, dog and human lung microsomes. The protocol for the studies with rat, dog, and human lung microsomes (from Xenotech, USA) is provided below.

0.4 mg protein was preincubated with 2 mM NADPH (cofactor) in phosphate buffer (pH~7.4) for 15 minutes at 370° C. and then added with 1 μM test item and incubated further for 60 minutes in triplicate. The reaction mixture was terminated with methanol containing an internal standard and centrifuged further to analyze the test item remaining in the supernatant by LC-MS/MS. The percent parent compound remaining was calculated in comparison with similar samples terminated at 0 minutes. Table 1 shows the lung metabolic stability data.

TABLE 1

| | Percent Parent Compound Remaining | | | | |
|---|---|---|---|---|---|
| Test Item | Rat | Dog | Human Smoker | Human Non Smoker | Additional Observation |
| Roflumilast | 97.1 | 97.4 | 98.8 | 99.8 | No N-Oxide Formation |
| Roflumilast-N-Oxide | 100.0 | 98.3 | 99.3 | 91.5 | No Roflumilast Formation |

Example 2: Pharmacokinetic (PK) Studies

Pulmonary Kinetics by Intratracheal (IT) Route

Male and female Wistar rats were weighed and randomized for groups for various time points. Roflumilast N-oxide was prepared as a suspension in a suitable vehicle for intratracheal administration. For intratracheal dosing, animals were anesthetized with ketamine (50 mg/kg; i.p.) and roflumilast N-oxide was administered via an Intratracheal Microsprayer® Aerosolizer for Rat with a 0.5 ml glass syringe (Model IA-1B-R-GL500) (Penn Century, US). A volume level of 0.5 ml/kg was administered into the airway system of the rat at a dose of 1.0 mg/kg for the single dose and multiple dose study. The animals were kept under normal regular diet conditions and rat chew diet was provided ad libitum throughout the study. The blood and lung samples (all collections each of 150 μl from each animal) were collected according to the sampling schedule. Blood samples were collected from orbital sinus into the microfuge tubes containing dipotassium EDTA as an anticoagulant. Blood samples were centrifuged immediately with a speed of 1000 g for 10 minutes at 4° C. and separated plasma samples were frozen at below −80° C. and stored until analysis. The plasma and lung concentrations of roflumilast N-oxide in all samples were analyzed by LC-MS/MS (using X-Calibur 2.0.7 software) as per the established method. The samples below the lower limit of quantification (LOQ) were mentioned as (BLQ) below level of quantification in raw data and the results were tabulated accordingly. Pharmacokinetic parameters $C_{max}$, $AUC_{0-t}$, $AUC_{0-\infty}$, $T_{max}$, $t_{1/2}$, Kel, VZ, and CLZ were estimated for the above concentrations using WinNonlin (Phoenix 6.1 software) and the results were tabulated. Pharmacokinetic parameters in plasma were calculated from concentration data as ng/ml. $C_{max}$ and AUC values were reported in terms of ng/ml and ng·h/ml, respectively.

Pharmacokinetic parameters in the lungs were calculated from concentration data as ng/g. $C_{max}$ and AUC values were reported in terms of ng/g and ng·h/g, respectively. The lung to plasma concentration ratio was calculated by assuming equal to 1 the plasma density. The time-mean plasma concentration plots for roflumilast N-oxide were done using Graph pad Prism 5.02 software. Table 2 shows the lung and plasma kinetics for the single and multiple dose studies.

For dry powder inhalation dosing, animals are anesthetised with ketamine (50 mg/kg; i.p.), then the animals are administered a mixture of micronized roflumilast N-oxide and a suitable carrier in a powder form via intratracheal insufflation (using a Penn Century insufflations powder delivery device (DP-4, US)).

Example 3A: In Vitro Biological Studies

Lipopolysaccharide (LPS) Induced TNFα in MH-S (Mouse Alveolar Macrophage) Cells:

MH-S represents a mouse alveolar macrophage cell line that secretes copious amounts of TNFα upon induction by LPS. Cells are plated at 150,000 cells per well. Different concentrations of roflumilast N-oxide are added 15 minutes prior to the addition of LPS. LPS (1 μg/ml) is added and then incubated for 4 hours. The supernatant is collected at the end of incubation period and TNFα estimated using an ELISA kit. Percent inhibition and $IC_{50}$ values are determined.

LPS Induced TNFα in THP-1 (Human Monocyte) Cells:

THP-1 represents a monocytic cell line that has elevated endogenous pAKT levels and secretes copious amounts of

TABLE 2

Single Dose
N = 3 for each time point at dose of 1 mg/kg of Roflumilast N-Oxide (IT)

| Parameter | Units | Lung | | Units | Plasma | |
|---|---|---|---|---|---|---|
| | | N-Oxide | Roflumilast | | N-Oxide | Roflumilast |
| $C_{max}$ | ng/g | 26350 | No | ng/ml | 530 | No |
| $AUC_{0-t}$ | ng · hr/g | 47880 | Formation | ng · hr/ml | 4160 | Formation |
| $AUC_{0-inf}$ | ng · hr/g | 47960 | | ng · hr/ml | 4350 | |
| $T_{max}$ | hr | 0.25 | | hr | 0.25 | |
| $t_{1/2}$ | hr | 2.54 | | hr | 5.43 | |

Multiple Dose
N = 3 for each time point at dose of 1 mg/kg of Roflumilast N-Oxide (IT) for 7 days

| Parameter | Units | Lung | | | | Units | Plasma | | | |
|---|---|---|---|---|---|---|---|---|---|---|
| | | Day-1 | | Day-7 | | | Day-1 | | Day-7 | |
| | | N-Oxide | Roflumilast | N-Oxide | Roflumilast | | N-Oxide | Roflumilast | N-Oxide | Roflumilast |
| $C_{min}$ | μg/g | — | No | 0.00 | No | μg/mL | — | No | 0.00 | No |
| $C_{avg}$ | μg/g | — | Formation | 0.77 | Formation | μg/mL | — | Formation | 0.12 | Formation |
| $C_{max}$ | μg/g | 26.35 | | 23.15 | | μg/mL | 0.53 | | 0.56 | |
| $AUC_{0-t}$ | μg · hr/g | 47.88 | | 17.96 | | μg · hr/mL | 4.16 | | 2.25 | |
| $AUC_{tau}$ | μg · hr/g | — | | 18.51 | | μg · hr/mL | — | | 2.81 | |
| $AUC_{0-inf}$ | μg · hr/g | 47.96 | | 18.04 | | μg · hr/mL | 4.35 | | 2.39 | |
| $T_{max}$ | hr | 0.25 | | 0.25 | | hr | 0.25 | | 1.00 | |
| $t_{1/2}$ | hr | 2.54 | | 0.81 | | hr | 5.43 | | 1.53 | |

Example 3: Inhalation Studies

For inhalation studies, roflumilast N-Oxide is administered as a suspension. Roflumilast N-oxide (100 mg) is placed in a mortar and triturated following addition of a suitable solvent in a gravimetric dilution to afford a fine suspension.

For inhalation suspension dosing, animals are placed in a plexiglass chamber and exposed to roflumilast N-oxide (at a suitable concentration) for a period of 30 minutes in an aerosol form using a Piston Nebulizer (Infi-Neb, USA) at an appropriate flow rate (L/min).

TNFα upon induction by LPS. Cells are plated at 150,000 cells per well. Different concentrations of roflumilast N-oxide are added. LPS (1 μg/ml) is added and then incubated for 4 hours. The supernatant is collected at the end of incubation period and TNFα estimated using an ELISA kit. Percent inhibition and $IC_{50}$ values are determined.

Con A+PMA induced IFNγ in Human Whole Blood:

Freshly collected human whole blood (HWB) is diluted with media and incubated with a desired concentration of inhibitor for 15 minutes. Cytokine release is induced with the addition of Concanavalin A (25 μg/ml)+Phorbol Myristate Acetate (50 ng/ml). The supernatant is collected after 20 hours and IFNγ estimated using an ELISA kit. Percent inhibition and $IC_{50}$ values are determined.

Con A+PMA Induced IFNγ in Peripheral Blood Mononuclear Cells (PBMC):

PBMC from whole blood are isolated by density gradient using Histopaque and incubated with a desired concentration of inhibitor for 15 minutes. Cytokine release is induced with the addition of Concanavalin A (25 µg/ml)+Phorbol Myristate Acetate (50 ng/ml). The supernatant is collected after 20 hours and IFNγ estimated using an ELISA kit. Percent inhibition and $IC_{50}$ values are determined.

Example 3B: In Vivo Biological Studies

A. Lipopolysaccharide (LPS) Induced Pulmonary Neutrophilia in a Female Sprague-Dawley Rat Model An exaggerated recruitment and subsequent activation of neutrophila is likely to be important for the development and course of several inflammatory diseases in the airways and lungs, such as severe asthma, chronic obstructive pulmonary disease, cystic fibrosis, and acute respiratory distress syndrome. The mechanisms by which neutrophila contribute to these diseases may involve the release of proteolytic enzymes, such as neutrophil elastase, and free oxygen radicals. When released, these compounds can cause bronchoconstriction, bronchial hyperreactivity, hyper-secretion, epithelial damage, and tissue remodelling in the airways.

Roflumilast was prepared as a suspension in a suitable vehicle for oral administration. For intratracheal administration, roflumilast or roflumilast N-oxide was prepared as a dry powder mixture and administered by using a dry powder Insufflator (Penn-Century, USA) Animals were anaesthetized with ketamine and LPS solution was administered intratracheally one hour after roflumilast (at a dose of 0.3, 1, 3, and 10 mg/kg orally), or 30 minutes after roflumilast (at a dose of 10, 30 and 100 µg/kg i.t) or roflumilast N-oxide administration (at a dose of 10, 30 and 100 µg/kg, i.t). 6 hours after LPS instillation, animals were exsanguinated under anaesthesia, and then trachea were cannulated and the lungs were lavaged with 5-ml aliquots of heparinised PBS (1 unit/ml) four times through tracheal cannula (total volume 20 ml). BAL (bronchoalveolar lavage) fluid was stored at 2-8° C. until assayed for total cell and differential leukocyte count. Bronchioalveolar fluid was centrifuged (500×g for 10 minutes) and the resulting cell pellet was resuspended in 0.5 ml of heparinized saline. The total number of white blood cells were determined in BAL fluid using a blood cell counter and were adjusted to $1 \times 10^6$ cell/ml. Differential cell count was calculated manually. One hundred microliters of the cell suspension was centrifuged using cytospin 3 to prepare a cell smear. The cell smear was stained with a blood staining solution for differentiation and slides were microscopically observed to identify eosinophil according to their morphological characteristics. The number of each cell type among 300 white blood cells in the cell smear was determined and expressed as a percentage. The total number of neutrophils in each BAL fluid was calculated.

Roflumilast and roflumilast N-oxide were administered intratracheally (i.t) at doses of 100, 30, and 10 µg/kg as 1:200; 1:500; and 1:1000 drug:lactose blends, respectively.

i. Effective Dose of Roflumilast

Roflumilast upon oral administration demonstrated a dose dependent inhibition in neutrophil infiltration compared to the control group at 0.3, 1, 3 and 10 mg/kg. The results are shown in FIG. 1. Percent inhibitions were −7.89%, 43.46%, 68.02%, and 92.21%, respectively, and the 50% inhibition ($ED_{50}$) dose was 1.8 mg/kg.

Figure 2:
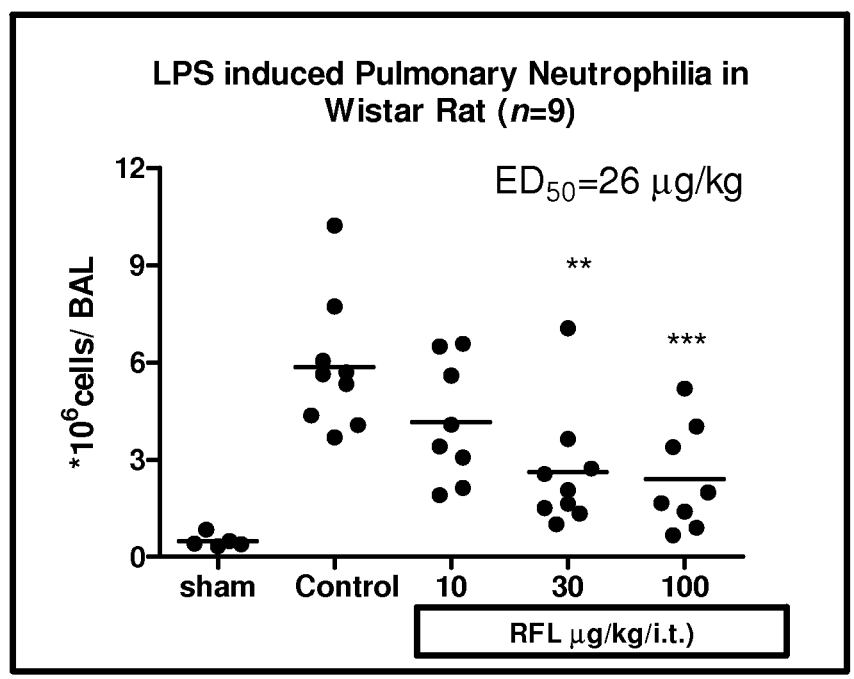
FIG. 2 is a scatter graph showing the effect of intratracheally (IT) administered roflumilast (RFL) (10, 30, and 100 µg/kg) on the inhibition of LPS-induced neutrophilia in the BALF of female Wistar rats (Example 3B.A).

Roflumilast upon intratracheal administration demonstrated a dose dependent inhibition in neutrophil infiltration compared to the control group at 10, 30 and 100 µg/kg. The results are shown in FIG. 2. Percent inhibitions were 31.76%, 60.47%, and 64.40%, respectively, and the 50% inhibition ($ED_{50}$) dose was 26 µg/kg.

ii. Effective Dose of Roflumilast N-Oxide

Figure 3:
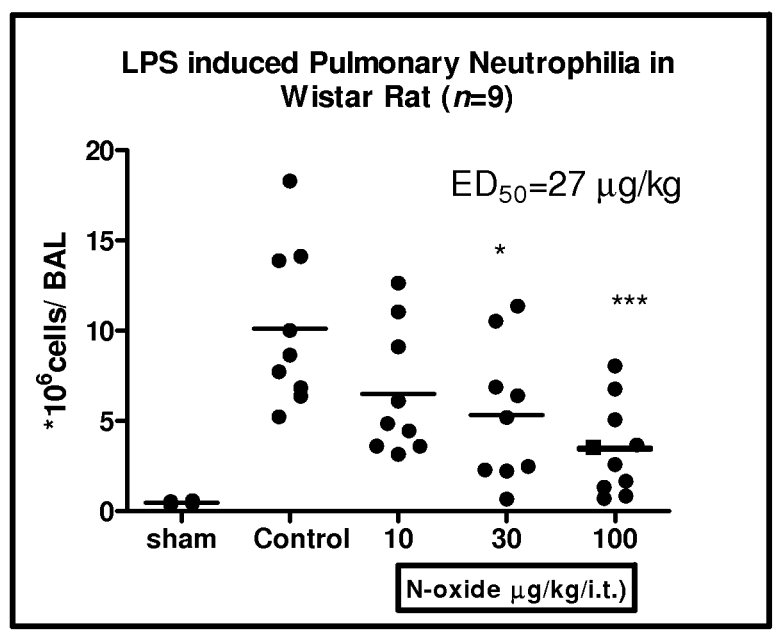
FIG. 3 is a scatter graph showing the effect of intratracheally (IT) administered roflumilast N-oxide (N-oxide) (10, 30, and 100 µg/kg) on the inhibition of LPS-induced neutrophilia in the BALF of female Wistar rats (Example 3B.A).

Roflumilast N-oxide upon intratracheal administration demonstrated a dose dependent inhibition in neutrophil infiltration compared to control group at 10, 30 and 100 µg/kg. The results are shown in FIG. 3. Percent inhibitions were 37.52%, 49.66%, and 69.48%, respectively, and the 50% inhibition ($ED_{50}$) dose was 27 µg/kg.

B. Acute Cigarette Smoke Induced Cell Infiltration in Female Balb/c Mice

Animals were acclimatized for seven days prior to the start of the experiment. The animals were randomly distributed to various groups based on their body weight. For oral administration of roflumilast and for intranasal administration of roflumilast N-oxide, roflumilast or roflumilast N-oxide were prepared as a suspension in a suitable vehicle. On day 1, mice were administered roflumilast N-oxide or roflumilast and after 1 hour, the animals were placed in a whole body exposure box. On day 1 and day 2, the mice were exposed to the mainstream smoke of 6 cigarettes, and 8 cigarettes on day 3 and day 4. Exposure to the smoke of each cigarette lasted for 10 minutes (cigarettes were completely burned in the first two minutes and followed by an air flow with animal ventilator, then 20 minutes exposure to fresh room air). After every second cigarette an additional break of 20 minutes with exposure to fresh room air was conducted. Control animals were exposed to room air chamber. From day 1 to day 4, the animals were administered roflumilast N-oxide or roflumilast. On day 5, 24 hours after the last cigarette smoke (CS) exposure, the animals were exsanguinated under anaesthesia, the trachea were cannulated and the lungs were lavaged with 0.5-ml aliquots of heparinised PBS (1 unit/ml) four times through tracheal cannula (total volume 2 ml). Bronchioalveolar (BAL) collected was stored at 2-8° C. until assayed for total cell and differential leukocyte count. BAL fluid was centrifuged (500×g for 10 minutes) and the resulting cell pellet was resuspended in 0.5 ml of heparinised saline. The total number of white blood cells was determined in BAL fluid and adjusted to $1 \times 10^6$ cell/ml. Differential cell count was calculated manually by diff-quick staining. Forty microliters of the cell suspension was centrifuged using cytospin 3 to prepare a cell smear. The cell smear was stained with a blood staining solution for differentiation and microscopically observed to identify cell type according to their morphological characteristics. The number of each cell type among 300 white blood cells in the cell smear were determined and expressed as a percentage, and the number of neutrophils and macrophages in each BAL fluid were calculated.

Roflumilast and roflumilast N-oxide as a suspension in polysorbate 80 (1% v/v) and methyl cellulose (MC) (0.5% w/v) were used for oral and intranasal administration respectively.

i. Effective Dose of Roflumilast

Figure 4A:
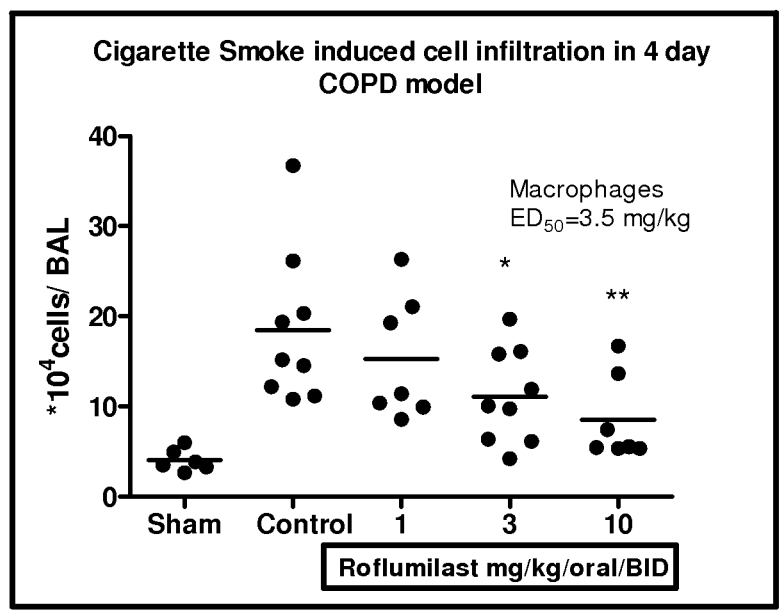
FIGS. 4A and 4B are scatter graphs showing the effect of orally administered roflumilast (RFL) (1, 3, and 10 mg/kg b.i.d.) observed in cigarette smoke induced cellular infiltration in BALB/c mice (Example 3B.B).
Figure 4B:
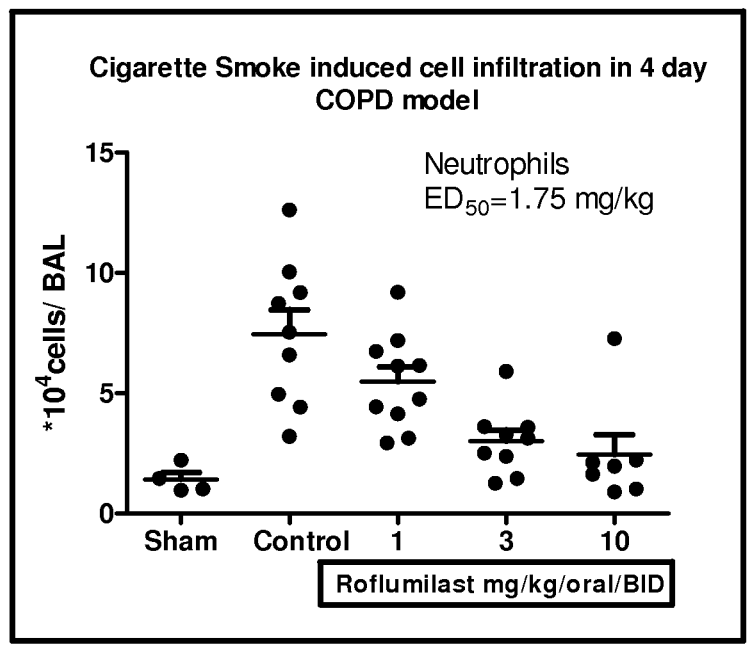

Roflumilast upon oral administration demonstrated a dose dependent inhibition in macrophage infiltration compared to control group at 1, 3 and 10 mg/kg. Percent inhibitions were 22.2%, 51.00%, and 69.11%, respectively, and the 50% inhibition ($ED_{50}$) dose was 3.5 mg/kg. Dose dependent inhibition in neutrophil infiltration was observed and the percent inhibitions were 70.85%, 73.69%, and 83.01% respectively, and the 50% inhibition ($ED_{50}$) dose was 1.75 mg/kg. The results for macrophages and neutrophils are shown in FIGS. 4A and 4B, respectively.

ii. Effective Dose of Roflumilast N-Oxide

Figure 5A:
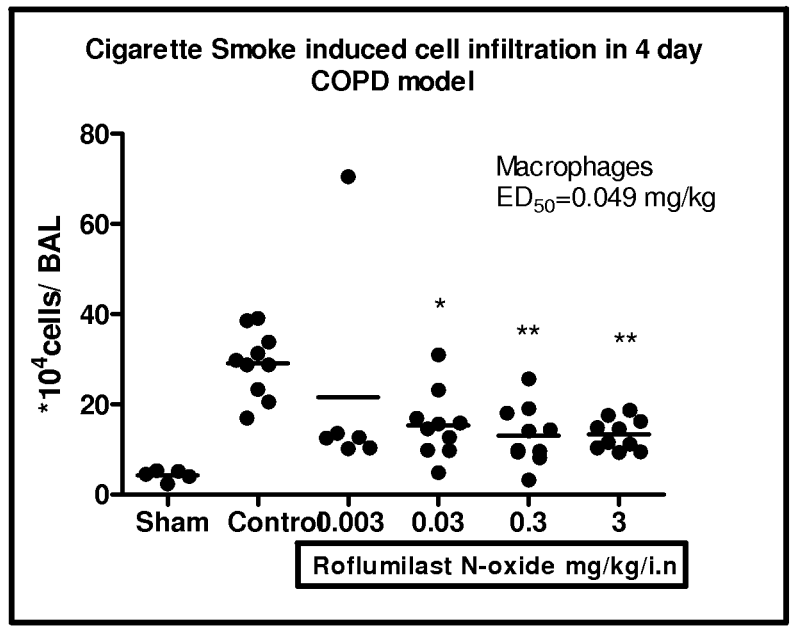
FIGS. 5A and 5B are scatter graphs showing the number of macrophages and neutrophils, respectively, in a 4 day cigarette smoke induced cellular infiltration COPD model following intranasally administered roflumilast N-oxide (N-oxide) (0.003, 0.03, 0.3, and 3 mg/kg intranasally) in BALB/c mice (Example 3B.B).
Figure 5B:
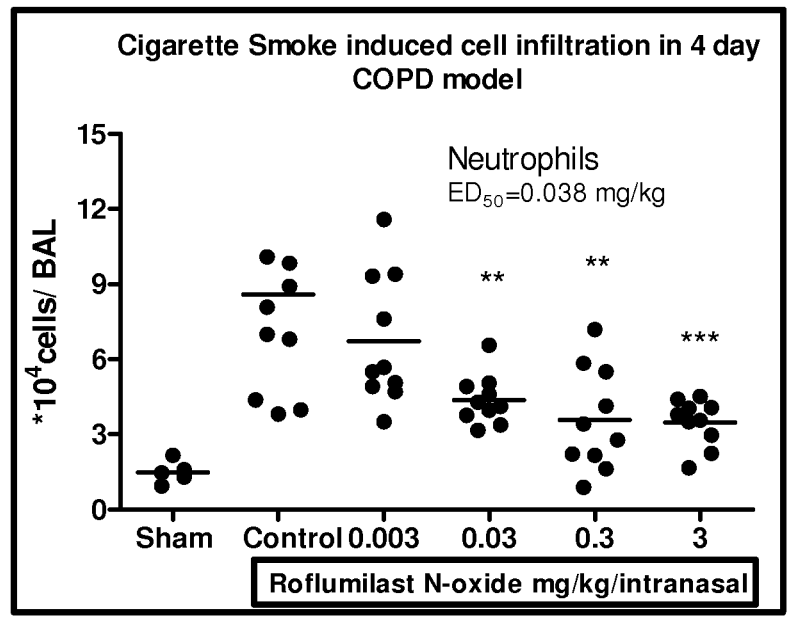

Roflumilast N-oxide upon intranasal administration demonstrated a dose dependent inhibition in macrophage infiltration compared to control group at 0.003, 0.03, 0.3 and 3 mg/kg. Percent inhibitions were 50.68%, 55.10%, 62.79% and 63.35%, respectively, and the 50% inhibition ($ED_{50}$) dose was 0.049 mg/kg. Dose dependent inhibition in neutrophil infiltration was observed and the percent inhibitions were 26.60%, 59.28%, 66.49% and 72.08% respectively. The 50% inhibition ($ED_{50}$) dose was 0.038 mg/kg. The results for macrophages and neutrophils are shown in FIGS. 5A and 5B, respectively.

C. Ovalbumin Induced Pulmonary Eosinophilia in Male Guinea Pigs

Airway inflammation and hyper-responsiveness (AHR) are hallmarks and distinguishing features of bronchial asthma. Provocation of pre-sensitized mice with the same allergen induces airway inflammation with preferential eosinophilic infiltration and, as a consequence, AHR. Pulmonary eosinophilia and airway remodelling in conjunction with altered neural control of airway tone and airway epithelial desquamation may contribute to AHR in asthma.

After the quarantine period, 0.3 mL blood samples are collected from orbital vein by retro-orbital plexus method from each individual animal and analysed on a cell analyser (ADVIA 2120, Siemens). Based on their total cell count, guinea pigs are randomized and divided into various groups. Ear pinna is marked with an indelible marking pen for identification. On day 0, weights are recorded and the animals are then sensitized with 50 µg of Ovalbumin and 10 mg of alum solution (1 mL) intraperitoneally. On day 7 and day 14, the above sensitization protocol is repeated. Roflumilast N-oxide is prepared as a suspension in a suitable vehicle or as a dry powder mixture. Roflumilast N-oxide or vehicle is administered by aerosol suspension or dry powder insufflation. On day 18, the animals are treated with roflumilast N-oxide. On days 19 and 20, the animals are treated with roflumilast N-oxide and exposed to 0.5% w/v ovalbumin for 10 minutes using an ultrasonic nebulizer with a flow rate of 0.2 ml per minute. On day 21, fasted animals are treated with roflumilast N-oxide and 15 minutes after dosing, animals are nebulized with 1% w/v ovalbumin solution for 10 min Control group animals are treated with 0.5% w/v methyl cellulose (vehicle). Sham control groups are sensitized with 10 mg of alum on days 0, 7 and 14 and exposed to saline solution with the same nebulization rate on days 19, 20 and 21. Twenty four hours after OVA challenge, blood samples and BAL fluid is collected. Samples are analysed for total cell count using a blood analyser (ADVIA 2120, Siemens) and differential leukocyte count is performed manually.

Example 4: Safety and Toxicity

In order to determine the safety of roflumilast N-oxide by inhalation compared to roflumilast by oral administration, a 7- and 14-day repeat dose safety study was conducted according to the protocol given in Table 5 below.

TABLE 5

| | | |
|---|---|---|
| Species: | Wistar Rats | |
| Experimental design | 5M + 5F - Main study and 5M + 5F in placebo groups | |
| Compound | Roflumilast N-Oxide | Roflumilast |
| Dose | 1000 ug/kg/day | 10 mg/Kg/day |
| Route | Intratracheal | Oral |
| ED50 in Lipopolysaccharide induced pulmonary neutrophilia in female Sprague-Dawley rat model | 27 ug/kg | 1.8 mg/kg |
| Criteria for Dose selection: | ~37 fold to ED50 of Roflumilast N-oxide | ~5.5 fold to ED50 of Roflumilast |
| Duration of the treatment: | 7 & 14 days for Roflumilast N-oxide | 7 days for Roflumilast |

The results are presented in Table 6.

TABLE 6

| | STUDY | | |
|---|---|---|---|
| | 7-DAY REPEAT DOSE | | 14-DAY REPEAT DOSE |
| | Drug & Route | | |
| PARAMETERS | Roflumilast by Oral* | Roflumilast N-Oxide by Intratracheal | Roflumilast N-Oxide by Intratracheal |
| CLINICAL SIGNS | Abnormal clinical signs were observed in treatment group animals compared to placebo group animals (abnormal gait) | No abnormal clinical signs were observed in treatment group animals compared to placebo group animals | No abnormal clinical signs were observed in treatment group animals compared to placebo group animals |
| MORTALITY | 1M animal died on day 7 | No Mortality | No Mortality |
| BODY WEIGHT PROFILE | Yes, significant reduction in body weight of around 25% observed in all treatment groups (n = 10) | No significant reduction in body weight observed at all treatment groups | No significant reduction in body weight observed at all treatment groups |
| HEMATOLOGY | Yes, elevated WBC with a corresponding lymphocytopenia | No treatment related changes observed across the groups. | No treatment related changes observed across the groups. |
| CLINICAL CHEMISTRY | Yes, reduced serum albumin and ALP, increases in total bilirubin | No abnormal clinical signs were observed in treatment group animals compared to | No abnormal clinical signs were observed in treatment group animals compared to |

TABLE 6-continued

| | STUDY | |
|---|---|---|
| | 7-DAY REPEAT DOSE | 14-DAY REPEAT DOSE |
| | Drug & Route | |
| PARAMETERS | Roflumilast by Oral* | Roflumilast N-Oxide by Intratracheal | Roflumilast N-Oxide by Intratracheal |
| ORGAN WEIGHTS | Yes, reduced thymus and spleen weight with an increase in weight of adrenals | placebo group animals No differences in the absolute and relative organ weight to body weight between control and treatment group animals | placebo group animals No differences in the absolute and relative organ weight to body weight between control and treatment group animals |
| GROSS PATHOLOGY | Yes, treatment related gross pathological changes including stomach enlargement | No treatment related gross pathological changes observed across the treatment groups | No treatment related gross pathological changes observed across the treatment groups |
| HISTOPATHOLOGY | Infiltration of neutrophils and mononuclear cells into lung alveolus observed indicating significant lung damage. Other changes included atrophy of thymus and spleen, hypertrophy/ hyperplasia of adrenals and gastric ulcerations. | No significant histopathological changes observed in lung, stomach, spleen, thymus and adrenal. | No significant histopathological changes observed in lung, stomach, spleen, thymus and adrenal |

Intratracheal administration of roflumilast N-oxide was found to be safe when compared to oral administration of roflumilast, which showed significant toxicity.

Intratracheal administration of roflumilast N-oxide (1000 µg/kg) was found to be safe and provide a significant therapeutic window of more than 37-fold based upon its $ED_{50}$ of 27 µg/kg. In contrast, oral administration of roflumilast (10 mg/kg) had a lower therapeutic index given its $ED_{50}$ of 1.8 mg/kg (i.e., it is toxic even at a 5.5 fold).

The preceding data on metabolic stability, pharmacokinetics, in vivo efficacy and safety studies related to roflumilast N-oxide demonstrates that administration of roflumilast N-oxide by inhalation has the desired therapeutic effect with significant improvements in safety when compared to oral administration of roflumilast.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications, patents and patent applications cited in this application are herein incorporated by reference to the same extent as if each individual publication, patent or patent application was specifically and individually indicated to be incorporated herein by reference.

What is claimed is:

1. A method of treating an autoimmune, respiratory or inflammatory disease or condition in a subject in need thereof comprising pulmonary administration of an effective amount of roflumilast N-oxide or a pharmaceutically acceptable salt thereof, wherein the $d_{50}$ of the roflumilast N-oxide or pharmaceutically acceptable salt thereof is less than about 6 microns, wherein the roflumilast N-oxide or pharmaceutically acceptable salt thereof is administered at a single dose of about 50 µg to about 1000 µg.

2. The method of claim 1, wherein the roflumilast N-oxide or pharmaceutically acceptable salt thereof is administered by inhalation.

3. The method of claim 1, wherein the roflumilast N-oxide or pharmaceutically acceptable salt thereof is administered by inhalation as a dry powder, solution or suspension.

4. The method of claim 3, wherein the roflumilast N-oxide or pharmaceutically acceptable salt thereof is administered as a dry powder.

5. The method of claim 3, wherein roflumilast N-oxide or pharmaceutically acceptable salt thereof is administered as a solution or suspension.

6. The method of claim 1, wherein the roflumilast N-oxide or pharmaceutically acceptable salt thereof is administered at a single dose of about 100 µg to about 800 µg.

7. The method of claim 1, wherein the roflumilast N-oxide or pharmaceutically acceptable salt thereof is administered at a single dose of about 100 µg, about 200 µg, about 400 µg, or about 600 µg.

8. The method of claim 1, wherein the disease or condition is selected from asthma, COPD, chronic obstructive bronchiolitis, acute bronchitis, chronic bronchitis, emphysema, allergic rhinitis and non-allergic rhinitis.

9. The method of claim 1, wherein the disease or condition is asthma.

10. The method of claim 1, wherein the disease or condition is COPD.

11. The method of claim 1, wherein the roflumilast N-oxide or pharmaceutically acceptable salt thereof is administered in combination with a long-acting µ2 agonist, an M3 antagonist, a corticosteroid, or any combination thereof.

12. The method of claim 11, wherein the long-acting β2 agonist is selected from carmoterol, GSK-642444, indacaterol, milveterol, arformoterol, formoterol, salbutamol, formoterol, levalbuterol, terbutaline, AZD-3199, BI-1744-CL, LAS-100977, bambuterol, isoproterenol, procaterol, clenbuterol, reproterol, fenoterol, ASF-1020, and any combination thereof.

13. The method of claim 11, wherein the M3 antagonist is selected from aclidinium, tiotropium, ipratropium and oxitropium, and any combination thereof.

14. The method of claim 11, wherein the corticosteroid is selected from the group consisting of dexamethasone, fluticasone, fluticasone furoate, prednisolone, betamethasone, budesonide, mometasone, mometasone furoate, triamcinolone acetonide, ciclesonide, TPI-1020, beclomethasone, beclomethasone dipropionate, prednisone, deflazacort, hydrocortisone, QAE-397, flunisolide, and any combination thereof.

15. The method of claim 1, wherein the roflumilast N-oxide or pharmaceutically acceptable salt thereof is anhydrous, a solvate, or a hydrate.

16. The method of claim 1, wherein the $d_{50}$ of the roflumilast N-oxide or pharmaceutically acceptable salt thereof is between about 0.5 and about 5 microns.

17. The method of claim 1, wherein the $d_{90}$ of the roflumilast N-oxide or pharmaceutically acceptable salt thereof is less than about 6 microns.

18. The method of claim 1, wherein the $d_{90}$ of the roflumilast N-oxide or pharmaceutically acceptable salt thereof is between about 0.5 and about 5 microns.

19. The method of claim 1, wherein the roflumilast N-oxide or pharmaceutically acceptable salt thereof is administered at a single dose of about 100 μg to about 1000 μg.

20. The method of claim 1, wherein the roflumilast N-oxide or pharmaceutically acceptable salt thereof is administered at a single dose of about 200 μg to about 400 μg.

21. The method of claim 1, wherein the roflumilast N-oxide or pharmaceutically acceptable salt thereof is administered at a single dose of about 200 μg to about 300 μg.

22. The method of claim 1, wherein the roflumilast N-oxide or pharmaceutically acceptable salt thereof is administered at a single dose of about 400 μg to about 600 μg.

23. A method of treating an autoimmune, respiratory or inflammatory disease or condition in a subject in need thereof comprising pulmonary administration of about 50 to about 1000 μg of roflumilast N-oxide or a pharmaceutically acceptable salt thereof.

24. The method of claim 23, wherein the $d_{50}$ of the roflumilast N-oxide or pharmaceutically acceptable salt thereof is less than about 6 microns.

25. The method of claim 23, comprising pulmonary administration of about 100 to about 1000 μg of roflumilast N-oxide or a pharmaceutically acceptable salt thereof.

* * * * *